(12) United States Patent
Nemoto et al.

(10) Patent No.: US 7,182,751 B2
(45) Date of Patent: Feb. 27, 2007

(54) LIQUID INJECTION SYSTEM WITH CYLINDER ADAPTER HOLDING CYLINDER FLANGE OF LIQUID SYRINGE WITH PAIR OF MOVABLE HOLDERS

(75) Inventors: Shigeru Nemoto, Tokyo (JP); Nobuhisa Tano, Tokyo (JP)

(73) Assignee: Nemoto Kyorindo Co., Ltd., Tokyo (JP)

( * ) Notice: Subject to any disclaimer, the term of this patent is extended or adjusted under 35 U.S.C. 154(b) by 209 days.

(21) Appl. No.: 10/857,404

(22) Filed: May 28, 2004

(65) Prior Publication Data

US 2004/0249276 A1 Dec. 9, 2004

(30) Foreign Application Priority Data

Jun. 9, 2003 (JP) ............................. 2003-163783

(51) Int. Cl.
*A61M 1/00* (2006.01)
(52) U.S. Cl. ................... 604/151; 128/DIG. 1
(58) Field of Classification Search ................ 604/131, 604/154, 155, 151; 128/DIG. 1, DIG. 12
See application file for complete search history.

(56) References Cited

U.S. PATENT DOCUMENTS

| 2,627,270 | A | * | 2/1953 | Glass ........................ 604/155 |
| 4,424,720 | A | * | 1/1984 | Bucchianeri ............. 74/424.78 |
| 4,838,857 | A | * | 6/1989 | Strowe et al. ................ 604/67 |
| 5,545,140 | A | * | 8/1996 | Conero et al. .............. 604/154 |
| 5,722,956 | A | * | 3/1998 | Sims et al. .................. 604/131 |
| 5,792,102 | A | * | 8/1998 | Muller-Spath ............... 604/70 |
| 6,974,443 | B2 | * | 12/2005 | Reilly et al. ................ 604/131 |
| 2001/0021823 | A1 | * | 9/2001 | Nemoto ...................... 604/154 |
| 2003/0040719 | A1 | | 2/2003 | Spohn et al. |
| 2003/0120212 | A1 | * | 6/2003 | Dedig et al. ................ 604/151 |
| 2004/0024361 | A1 | | 2/2004 | Fago et al. |

FOREIGN PATENT DOCUMENTS

| EP | 1 123 712 A1 | 8/2001 |
| JP | 2002-11096 | 1/2002 |
| JP | 2002-102343 | 4/2002 |
| WO | WO 02/056947 A | 7/2002 |

* cited by examiner

*Primary Examiner*—Sharon E. Kennedy
(74) *Attorney, Agent, or Firm*—Knobbe Martens Olson & Bear, LLP

(57) ABSTRACT

A cylinder adapter holds a cylinder flange of a liquid syringe with movable holders that are selectively openable and closable. The cylinder adapter can reliably hold the liquid syringe.

17 Claims, 6 Drawing Sheets

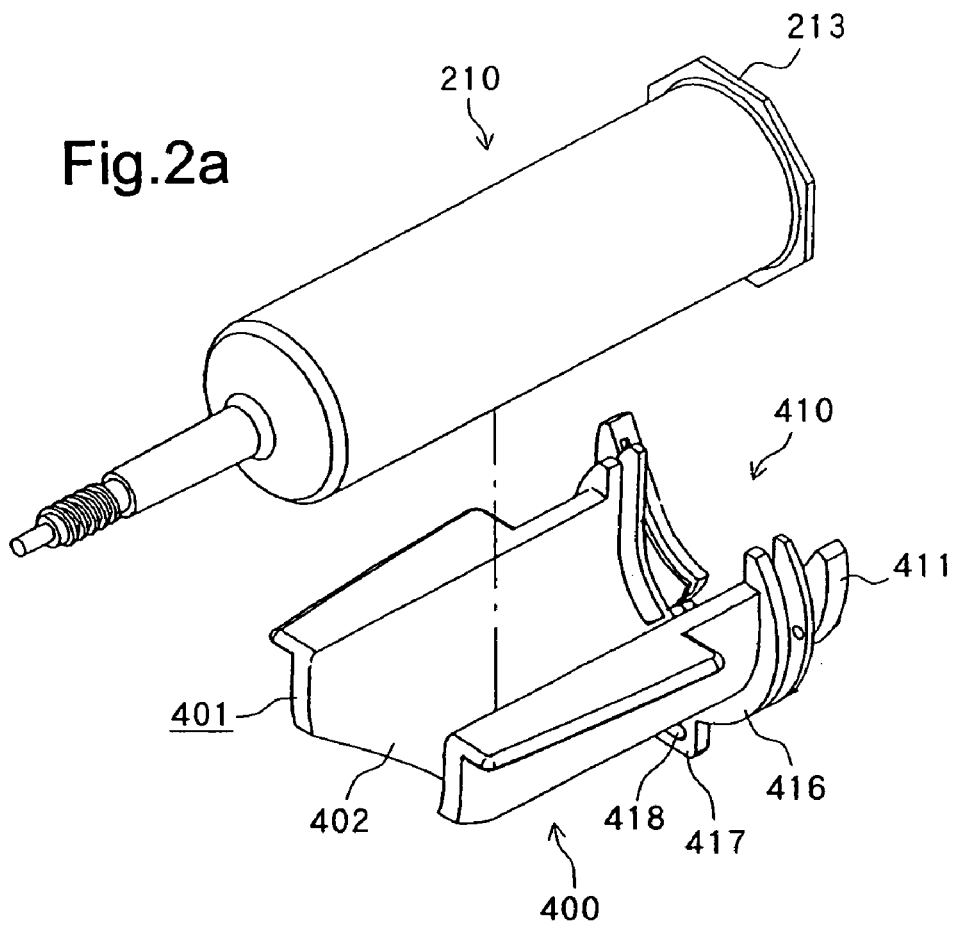
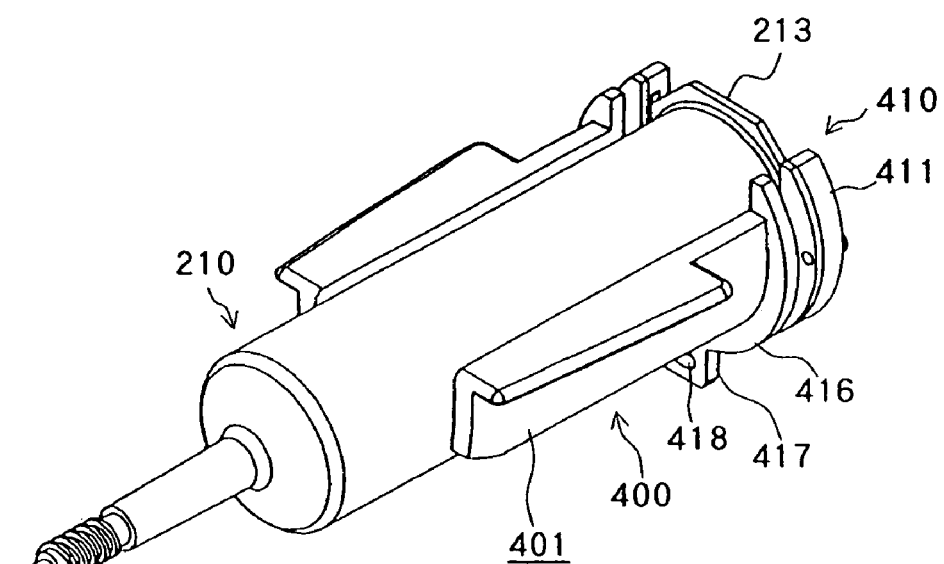

LIQUID INJECTION SYSTEM WITH CYLINDER ADAPTER HOLDING CYLINDER FLANGE OF LIQUID SYRINGE WITH PAIR OF MOVABLE HOLDERS

BACKGROUND OF THE INVENTION

1. Field of the Invention

The present invention relates to a liquid injection system for injecting liquid into a patient by relatively moving a cylinder and a piston of a liquid syringe that is mounted on a liquid injector, and more particularly relates to a liquid injection system in which a liquid syringe is mounted on a liquid injector by a cylinder adapter.

2. Description of the Related Art

Presently available imaging diagnostic apparatus for capturing fluoroscopic images of patients include CT (Computed Tomography) scanners, MRI (Magnetic Resonance Imaging) apparatus, PET (Positron Emission Tomography) apparatus, ultrasonic diagnostic apparatus, angiography apparatus, and MRA (MR Angiography) apparatus.

When such imaging diagnostic apparatus are used to capture a fluoroscopic image of a patient, it is occasionally practiced to inject a liquid such as a contrast medium or a saline solution into the patient. This liquid injector for automatically injecting a liquid into a patient has practical application. Such a liquid injector has a main injector body on which a liquid syringe is removably mounted.

The liquid syringe has a hollow cylinder filled with a liquid and a cylindrical piston slidably inserted in the cylinder. Generally, the cylinder has an annular cylinder flange disposed on the outer circumferential edge of the rear end thereof, and the piston has an annular piston flange disposed on the outer circumferential edge of the rear end thereof.

When the liquid injector is in use, the cylinder of the liquid syringe which is filled with the liquid is connected to the patient by an extension tube, and the liquid syringe is mounted on the main injector body. In general liquid injectors, the main injector body has a recess defined in its upper surface complementary in shape to the cylinder of the liquid syringe and its cylinder flange. Therefore, the liquid syringe is held on the main injector body when the cylinder and the cylinder flange are placed in the recess.

The liquid injector also has a syringe actuating mechanism for holding the piston flange independently of the cylinder and sliding the piston into and out of the cylinder. When the piston is pushed into the cylinder, the liquid in the cylinder can be injected into the patient. When the piston is pulled out of the cylinder, the cylinder can draw the liquid from a liquid container.

Generally, in order to allow the liquid injector to hold a various types of liquid syringes having various shapes, the recess defined in the upper surface of the main injector body is shaped to be able to receive the cylinder of the liquid syringe having the maximum size. Liquid syringes having sizes other than the maximum size are combined with respective dedicated cylinder adapters and placed in the recess in the main injector body.

Cylinder adapters generally have recesses defined in their upper surfaces complementary in shape to the cylinders of the liquid syringes and their cylinder flanges. The cylinders of the liquid syringes and their cylinder flanges are held in the recesses in the cylinder adapters. The cylinder adapters have lower surfaces whose outer profiles are similar to the outer profile of the cylinder of the liquid syringe having the maximum size and the cylinder flange thereof, and are placed in the recess in the main injector body.

Liquid injectors constructed as described above have been invented by the inventor of the present invention and filed for patent (see, for example, Patent documents 1 and 2 shown below):

Patent document 1: Japanese laid-open patent publication No. 2002-11096.

Patent document 2: Japanese laid-open patent publication No. 2002-102343.

The above liquid injectors hold a liquid syringe when the cylinder is directly placed in the recess in the main injector body or when the cylinder adapter with the cylinder mounted in its recess is placed in the recess in the main injector body.

However, since the liquid syringe or the cylinder adapter is merely placed in the recess in the main injector body, it is difficult to keep the liquid syringe or the cylinder adapter securely retained in the recess. As a result, the liquid syringe or the cylinder adapter may possibly be incompletely be retained in the recess, and hence may possibly be dislodged from the recess while the liquid is being injected from the liquid syringe into the patient.

One liquid injector that has been proposed to solve the above problems has a clamp mechanism disposed in the recess in the main injector body for clamping the cylinder flange of a liquid syringe or the adapter flange of a cylinder adapter.

However, even the proposed liquid injector fails to reliably hold liquid syringes because the cylinder adapters simply hold corresponding liquid syringes by placing them in recesses defined in the cylinder adapters.

SUMMARY OF THE INVENTION

It is therefore an object of the present invention to provide a liquid injection system which allows a cylinder adapter to hold a liquid syringe securely and reliably.

A liquid injection system according to the present invention has liquid syringes in various sizes and/or shapes, at least one size and/or shape of cylinder adapter, and a single liquid injector. Each of the liquid syringes has a hollow cylinder with a cylinder flange disposed on the outer circumferential edge of an end thereof and a piston slidably inserted in the cylinder though a cylinder opening defined in the opposite end of the cylinder. The cylinder adapter is arranged to receive the cylinder of at least one of the liquid syringes which is placed from above into the cylinder adapter. The liquid injector is arranged to separately hold the cylinder of the liquid syringe received by the cylinder adapter and the piston thereof, the liquid injector having a syringe actuating mechanism for moving the cylinder and the piston relatively to each other in longitudinal axial directions thereof.

The cylinder adapter of the liquid injection system has an adapter body, a pair of laterally spaced movable holders, and holder pivot support mechanisms. The adapter body has a recess for receiving the cylinder which is removably placed from above into the adapter body. The movable holders have arcuate grooves defined in inner edges thereof for disengageably receiving the cylinder flange of the liquid syringe which extends in the longitudinal axial directions. The movable holders are pivotally supported by the holder pivot support mechanisms for vertical angular movement between an open position in which the movable holders are open upwardly for allowing the cylinder flange to be inserted into the grooves, and a closed position in which the cylinder flange is retained at opposite sides thereof in the grooves.

With the liquid injection system according to the present invention, as the cylinder adapter holds the cylinder flange of the liquid syringe with the movable holders that are selectively openable and closable, the cylinder adapter can reliably hold the liquid syringe.

Various means referred to in the present invention may be arranged to perform their functions, and may comprise dedicated hardware for performing a predetermined function, a data processing apparatus whose predetermined function is given by a computer program, a predetermined function performed by a data processing apparatus according to a computer program, or a combination thereof.

Various components referred to in the present invention do not need to be a separate entity. Rather, these components may be constructed as one component, a certain component may be part of another component, or a certain component may have a portion overlapping a portion of another component.

Certain terms with respect to forward, rearward, upward, downward, leftward, and rightward directions which will be referred to in the description are used for convenience only to simplify the illustration of relative positional relationships of various parts, and should not be interpreted as being limited to directions that are involved when the liquid injection system is manufactured and used.

The above and other objects, features, and advantages of the present invention will become apparent from the following description with reference to the accompanying drawings which illustrate examples of the present invention.

BRIEF DESCRIPTION OF THE DRAWINGS

FIGS. 2a and 2b are perspective views showing the manner in which the liquid syringe is mounted on the cylinder adapter;

DETAILED DESCRIPTION OF THE PREFERRED EMBODIMENTS

Figure 1A:
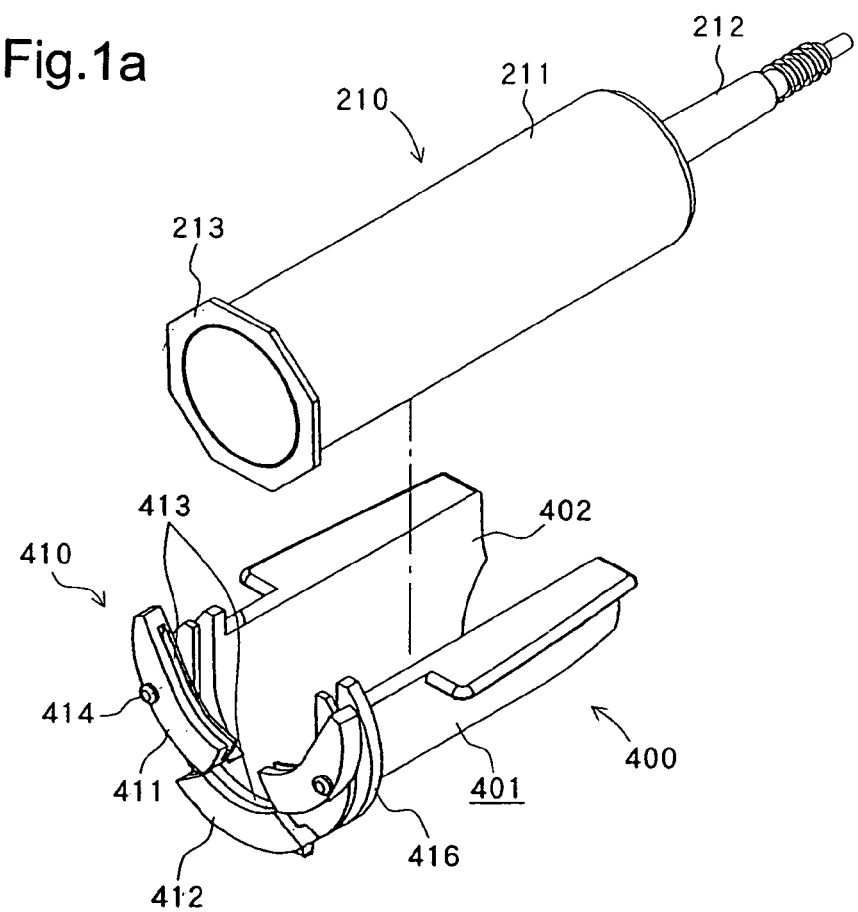
FIGS. 1a and 1b are perspective views showing the manner in which a liquid syringe is mounted on a cylinder adapter of a liquid injection system according to the present invention.
Figure 1B:
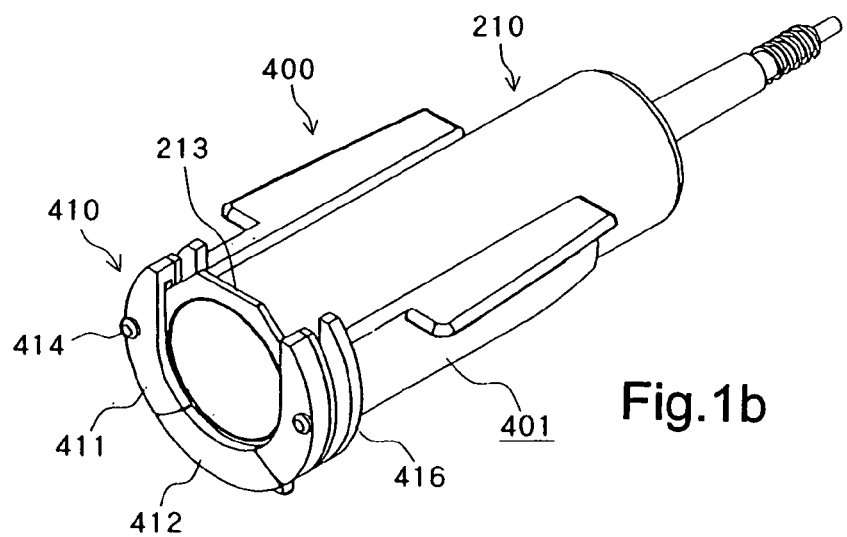
Figure 3:
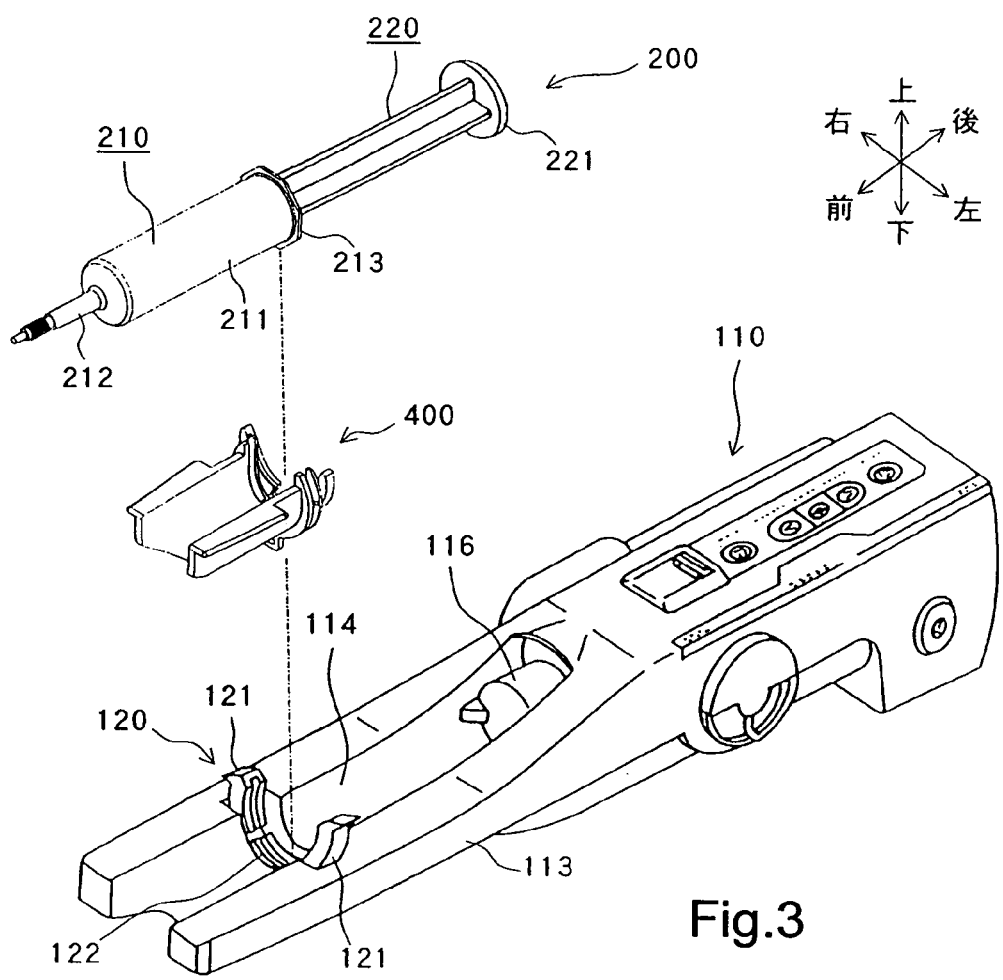
FIG. 3 is an exploded perspective view showing the manner in which a liquid syringe is mounted on a liquid injector by a cylinder adapter.
Figure 4:
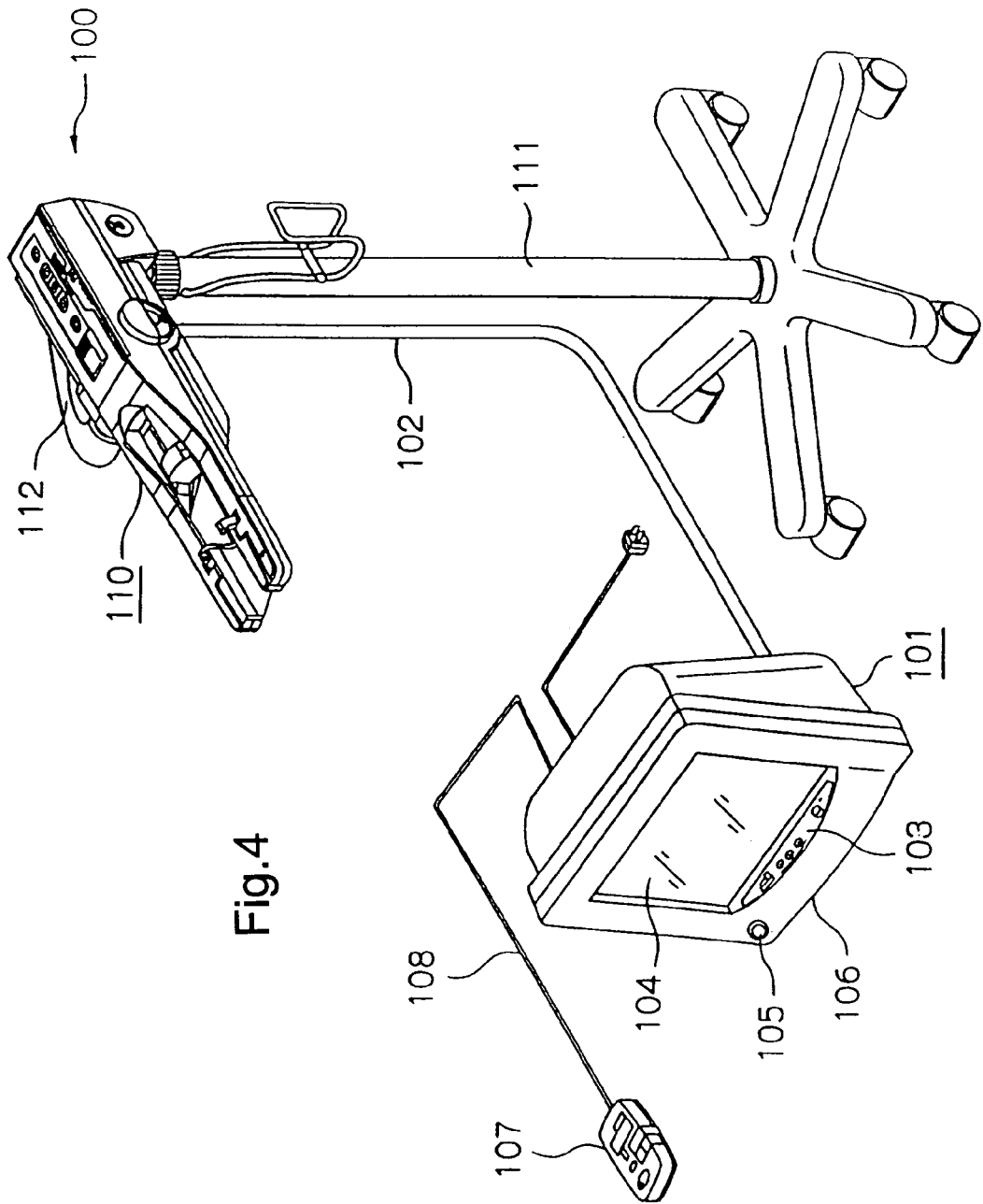
FIG. 4 is a perspective view of the liquid injector.
Figure 5:
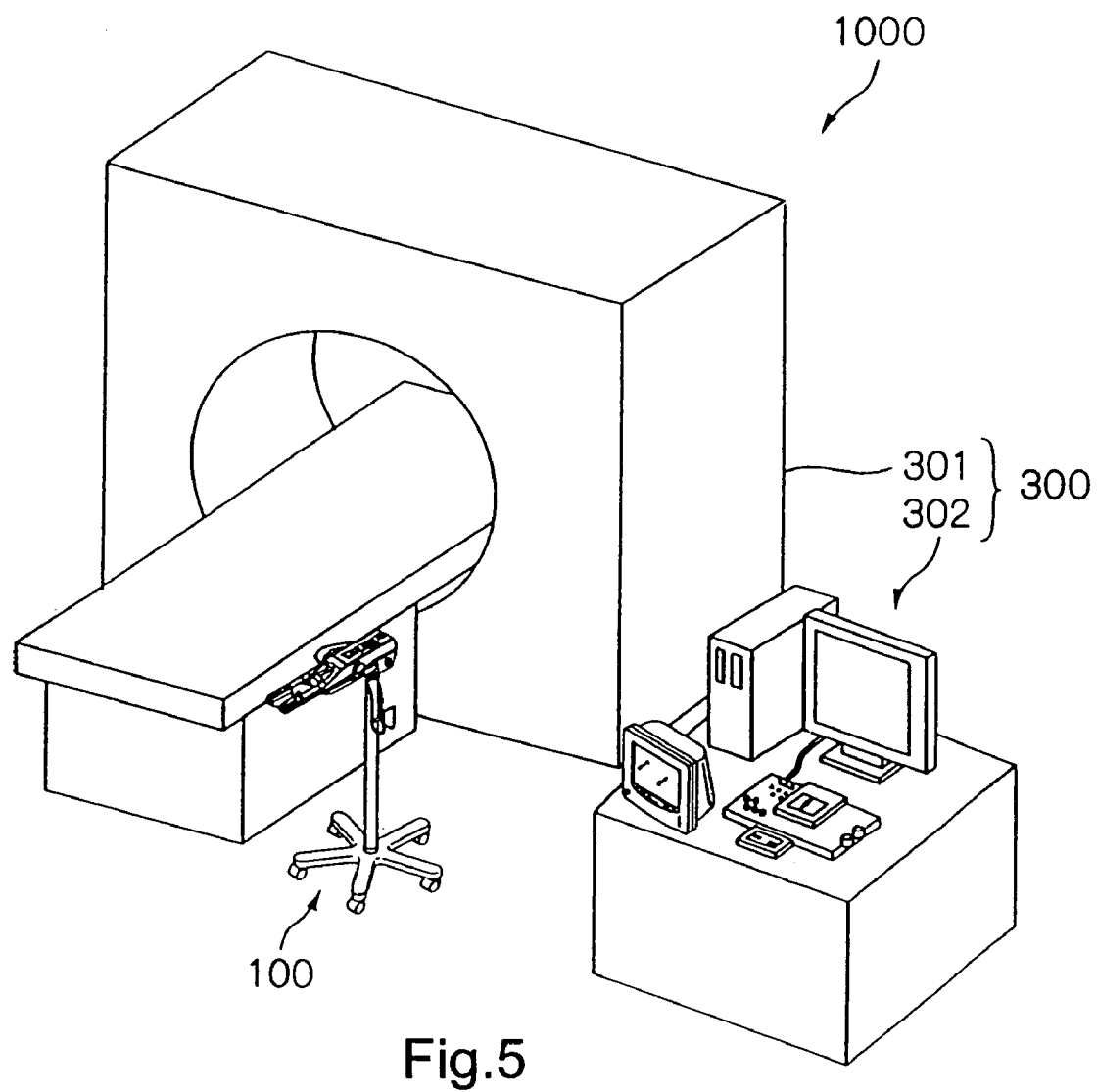
FIG. 5 is a perspective view of the liquid injection system.

A liquid injection system according to the present invention will be described below with reference to the accompanying drawings. Structure of the liquid injection system:

As shown in FIGS. 3 through 5, liquid injection system 1000 according to the present invention has liquid injector 100, liquid syringe 200, MRI apparatus 300 as an imaging diagnostic apparatus, and cylinder adapter 400. When a fluoroscopic image of a patient (not shown) is to be captured by MRI apparatus 300, liquid injector 100 injects a liquid such as a contrast medium or a saline solution from liquid syringe 200 into the patient.

As shown in FIG. 5, MRI apparatus 300 comprises imaging unit 301 as an image capturing mechanism and control unit 302 which are connected to each other by a wired communication network (not shown). Imaging unit 301 captures a tomographic image of the patient, and control unit 302 controls operation of imaging unit 301.

As shown in FIG. 3, liquid syringe 200 comprises cylinder 210 and piston 220 slidably inserted in cylinder 210. Cylinder 210 has hollow cylindrical cylinder casing 211 with conduit 212 disposed on a closed distal end thereof.

Cylinder casing 211 has an open end remote from the closed distal end thereof, and piston 220 is inserted into cylinder casing 211 through the open end. Cylinder casing 211 has cylinder flange 213 disposed on the outer circumferential edge of the open end thereof. Piston 220 has piston flange 221 disposed on the outer circumferential edge of an end thereof.

As shown in FIG. 4, liquid injector 100 comprises injection control unit 101 and injection head 110 as a main injector body which are separate from each other. Injection control unit 101 and injection head 110 are connected to each other by communication cable 102.

Injection head 110 actuates liquid syringe 200 mounted thereon to inject a liquid therefrom into the patient. Injection control unit 101 controls the operation of injection head 110. Injection control unit 101 houses a microcomputer (not shown) therein, and is connected to control unit 302 of MRI apparatus 300 by the wired communication network (not shown).

Injection control unit 101 has console panel 103, touch panel 104 as a display panel, and speaker unit 105 which are disposed on the front face of a unit housing 106. Separate controller unit 107 is connected to main injector unit 101 by connector 108.

Injection head 110 is mounted on the upper end of caster stand 111 by movable arm 112. As shown in FIG. 3, injection head 110 includes head body 113 having semi-cylindrical groove-like recess 114 defined in an upper surface thereof for receiving liquid syringe 200 removably mounted therein.

Injection head 110 has syringe actuating mechanism 116 positioned rearwardly of recess 114 for holding piston flange 221, and flange holding mechanism 120 disposed forwardly of recess 114 for removably holding cylinder flange 213 of liquid syringe 200.

Syringe actuating mechanism 116 has an ultrasonic motor (not shown) as a drive source which does not produce a magnetic field. The ultrasonic motor is made of a nonmagnetic material such as phosphor bronze alloy (Cu+Sn+P), titanium alloy (Ti–6Al–4V), magnesium alloy (Mg+Al+Zn), or the like.

Liquid injection system 1000 has liquid cylinders 200 available for use in various different sizes. Only liquid syringe 200 having the maximum size is directly mounted in recess 114 in injection head 110, and other liquid syringes 200 having sizes other than the maximum size are selectively mounted in recess 114 with respective dedicated cylinder adapters 400.

Flange holding mechanism 120 of liquid injector 100 is of a structure for holding cylinder flange 213 of a liquid syringe having the maximum size. Cylinder adapter 400 has an outer profile which is of the same shape as liquid syringe 200 having the maximum size so that cylinder adapter 400 can be held by recess 114 and flange holding mechanism 120 of injection head 110.

Flange holding mechanism 120 has a pair of laterally spaced movable holders 121 and a single stationary holder 122 disposed between movable holders 121. Movable holders 121 and stationary holder 122 are disposed in an annular pattern. Stationary holder 122 has a semi-arcuate shape which is upwardly concave, and movable holders 121, each of a quarter arcuate shape, are disposed one on each side of stationary holder 122.

Movable and stationary holders 121, 122 have respective grooves defined in inner concave edges thereof. Cylinder flange 213 of liquid syringe 200 having the maximum size engages removably in the grooves in movable and stationary holders 121, 122. Movable holders 121 are pivotally supported by respective holder pivot support mechanisms (not shown) for vertical angular movement between an open position in which movable holders 121 are open upwardly for allowing cylinder flange 213 to be inserted into the grooves in movable and stationary holders 121, 122, and a closed position in which cylinder flange 213 is retained at its opposite sides in the grooves in movable and stationary holders 121, 122.

Movable holders 121 are normally biased into the open position by holder biasing mechanisms (not shown) that are connected respectively to movable holders 121. When movable holders 121 are in the closed position, their lower ends are positioned downwardly of the axes of the holder pivot support mechanisms and their upper ends are positioned upwardly of the axes of the holder pivot support mechanisms. Movable holders 121 are constructed as components separate from head body 113. However, movable holders 121 may be integrally formed with head body 113.

Cylinder adapters 400 are available for use with respective liquid syringes 200 having sizes other than the maximum size. As shown in FIGS. 1a, 1b and 2a, 2b, each cylinder adapter 400 has adapter body 401 that is curved into a U shape. Adapter body 401 has recess 402 of a U-shaped cross section which is defined therein for receiving cylinder 210 of liquid syringe 200 that is removably placed from above into adapter body 401. Cylinder adapter 400 has flange holding mechanism 410 disposed behind recess 402 for holding liquid syringe 200.

Flange holding mechanism 410 of cylinder adapter 400 is of a structure similar to flange holding mechanism 120 of liquid injector 100. Specifically, flange holding mechanism 410 has a pair of laterally spaced movable holders 411 and a single stationary holder 412 disposed between movable holders 411. Movable holders 411 and stationary holder 412 have respective grooves 413 defined in inner concave edges thereof. Cylinder flange 213 of liquid syringe 200 engages removably in grooves 413. Movable holders 411 are supported by respective holder pivot support mechanisms 414 for vertical angular movement between an open position in which movable holders 411 are open upwardly for allowing cylinder flange 213 to be inserted into grooves 413, and a closed position in which cylinder flange 213 is retained at its opposite sides in grooves 413.

When movable holders 411 are in the closed position, their lower ends are positioned downwardly of the axes of holder pivot support mechanisms 414 and their upper ends are positioned upwardly of the axes of holder pivot support mechanisms 414. Stationary holder 412 is integrally formed with adapter body 401. However, stationary holder 412 may be constructed as a component separate from adapter body 401.

Adapter body 401 has a lower surface whose outer profile is similar to the outer profile of cylinder 210 of liquid syringe 200. Adapter body 410 has adapter flange 416 disposed on the lower surface thereof forward of the flange holding mechanism 410. Adapter flange 416 has an outer profile which is the same as the outer profile of cylinder flange 213 of liquid cylinder 200 having the maximum size.

Adapter body 401 has connector lug 417 projecting downwardly from a rear portion of the lower surface thereof, i.e., from the lower end of adapter flange 416. Connector lug 417 has connector hole 418 defined therein which is open in the longitudinal axial direction of cylinder adapter 400. Liquid injector 100 has a connector member (not shown) disposed on the bottom of recess 114 and supported by a member support mechanism (not shown) for movement in the longitudinal direction of groove-like recess 114. The connector member can removably engage in connector hole 418 in connector lug 417 of cylinder adapter 400 when cylinder adapter 400 is mounted in recess 114.

The connector member may be in the form of an engaging finger, for example, and is normally biased forwardly by a resilient mechanism such as a spring or the like. The connector member has an integral manually operable member (not shown) which is exposed on the lower surface of injection head 110.

As shown in FIGS. 1a, 1b and 2a, 2b, movable holders 411 of cylinder adapter 400 project radially outwardly when they are in the open position. Therefore, while cylinder adapter 400 with movable holders 411 in the closed position can be installed in recess 114 in injection head 110, cylinder adapter 400 with movable holders 411 in the open position cannot be installed in recess 114 in injection head 110.

Adapter body 401 and movable holders 411 are made of engineering plastic, and holder pivot support mechanisms 414 are made of a nonmagnetic material such as phosphor bronze alloy (Cu+Sn+P), titanium alloy (Ti–6Al–4V), magnesium alloy (Mg+Al+Zn), or the like. Therefore, cylinder adapter 400 is made of nonmagnetic materials.

Operation of the Liquid Injection System:

The liquid injection system 1000 according to the present invention operates as follows: The operator selects liquid syringe 200 that is suitable for a liquid that is to be injected into the patient, and connects conduit 212 of selected liquid syringe 200 to the patient with an extension tube (not shown).

If selected liquid syringe 200 is of the maximum size which does not require the use of cylinder adapter 400, then cylinder 210 thereof is directly placed in recess 112 in injection head 110, and cylinder flange 213 is held by flange holding mechanism 120 and piston 220 is simultaneously gripped by cylinder actuating mechanism 116.

If selected liquid syringe 200 is of a size other than the maximum size, then, as shown in FIGS. 1a, 1b and 2a, 2b, liquid syringe 200 is mounted on cylinder adapter 400, and then placed together with cylinder adapter 400 on injection head 110.

More specifically, if movable holders 411 of cylinder adapter 400 are in the open position, then when cylinder 210 of liquid cylinder 200 is inserted from above into recess 402 to insert cylinder flange 213 into grooves 413, movable holders 411 are automatically turned into the closed position by being pressed by cylinder 210. Cylinder flange 213 of liquid syringe 200 is now retained at its opposite sides by movable holders 411 of cylinder adapter 400, and retained at its lower side by stationary holder 412.

Then, liquid syringe 200 is inserted, together with cylinder adapter 400, from above into recess 114 in injection head 110. Movable holders 121 that are in the open position are automatically turned into the closed position. Adapter flange 416 is now retained at its opposite sides by movable holders 121, and retained at its lower side by stationary holder 122.

At this time, the connector member of liquid injector 100 engages in connector hole 418 in connector lug 417 of cylinder adapter 400, thus fixing cylinder adapter 400 to injection head 110. With cylinder adapter 410 mounted in recess 114 in injection head 110, movable holders 411 are held against the inner surface of recess 114 and hence can not be opened.

When liquid syringe 200 is thus mounted on liquid injector 100 with cylinder adapter 400, cylinder adapter 400 is secured to liquid injector 100, and liquid syringe 200 is secured to cylinder adapter 400. Therefore, liquid syringe 200 is secured to liquid injector 100.

For removing liquid syringe 200 from liquid injector 100, the manually operable member exposed on the lower surface of injection head 110 is manually operated to disengage the connector member from connector lug 417 of cylinder adapter 400. Movable holders 121 are now turned from the closed position to the open position under the bias of the holder biasing mechanisms.

As cylinder adapter 400 is pushed upwardly by the lower portions of movable holders 121, liquid syringe 200 and cylinder adapter 400 are easily dislodged from injection head 110. When cylinder adapter 400 is dislodged from injection head 110, movable holders 411 can now be turned, allowing liquid syringe 200 to be easily removed from cylinder adapter 400.

Advantages of the Liquid Injection System:

With liquid injection system 1000, liquid syringe 200 having the maximum size can be directly installed in liquid injector 100, and liquid syringes 200 having sizes other than the maximum size can be installed in liquid injector 100 with respective dedicated cylinder adapters 400.

Since cylinder adapter 400 holds cylinder flange 213 of liquid syringe 200 with the pair of movable holders 411, liquid syringe 200 can easily be mounted on and dismounted from cylinder adapter 400, and cylinder adapter 400 can reliably hold liquid syringe 200.

As liquid injector 100 holds adapter flange 416 of cylinder adapter 400 with movable holders 121 which are angularly movable, cylinder adapter 400 can easily be mounted on and dismounted from liquid injector 100, and liquid injector 100 can reliably hold cylinder adapter 400.

Consequently, even if liquid syringe 200 is mounted on liquid injector 100 with cylinder adapter 400, liquid syringe 200 can reliably be held by liquid injector 100. In particular, inasmuch as the connector member of liquid injector 100 engages in connector hole 418 of cylinder adapter 400, cylinder adapter 400 can reliably be fixed to liquid injector 100.

When the cylinder adapter 400 is not being installed in liquid injector 100, movable holders 411 are angularly movable about respective holder pivot support mechanisms 414. However, when the cylinder adapter 400 is installed in liquid injector 100, movable holders 411 are held in the closed position. Therefore, liquid syringe 200 can be reliably secured to cylinder adapter 400 that is mounted on liquid injector 100.

When movable holders 411 are held in the closed position, cylinder adapter 400 can be installed in liquid injector 100. However, when movable holders 411 are held in the open position, cylinder adapter 400 cannot be installed in liquid injector 100. Consequently, cylinder adapter 200 can not be installed in liquid injector 100 insofar as liquid syringe 200 is incompletely held by movable holders 411.

When movable holders 411 of cylinder adapter 400 are in the closed position, the lower ends of movable holders 411 are positioned below the axes of holder pivot support mechanisms 414 and the upper ends of movable holders 411 are positioned above the axes of holder pivot support mechanisms 414. Therefore, when liquid cylinder 200 is inserted from above into cylinder adapter 400 with movable holders 411 in the open position, movable holders 411 are automatically turned into the closed position.

When liquid cylinder 200 is pulled upwardly from cylinder adapter 400 with movable holders 411 in the closed position, movable holders 411 are automatically turned into the open position. Thus, liquid syringe 200 can easily and intuitively be placed in and removed from cylinder adapter 400. Movable holders 121 of liquid injector 100 and cylinder adapter 400 also operate in the same fashion, so that cylinder adapter 400 can easily and intuitively be mounted on and removed from liquid injector 100.

When cylinder actuating mechanism 116 presses piston 220 of liquid syringe 200, large stresses are applied to cylinder flange 213 and adapter flange 416. However, since cylinder flange 213 and adapter flange 416 have their lower portions held by stationary holders 412, 122, respectively, cylinder flange 213 and adapter flange 416 are firmly retained in place.

With liquid injection system 1000, liquid injector 100 is used in the vicinity of MRI apparatus 300. Since the drive source of liquid injector 100 comprises an ultrasonic motor made of a nonmagnetic material which does not produce a magnetic field, and the components of cylinder adapter 400 are made of a nonmagnetic material, liquid injector 100 and cylinder adapter 400 can be used in the vicinity of MRI apparatus 300 without any problems. Modification of the liquid injection system:

The present invention is not limited to the above embodiment, but various changes and modifications may be made therein without departing from the scope of the invention.

For example, although it is assumed in the above embodiment that liquid injector 100 is used in the vicinity of MRI apparatus 300, liquid injector 100 may also be used in the vicinity of a CT scanner or an angiography apparatus.

In the above embodiment, liquid syringe 200 having the maximum size is directly mounted on liquid injector 100 and liquid syringes 200 having sizes other than the maximum size are selectively mounted on liquid injector 100 with respective cylinder adapters 400. However, all liquid syringes 200 may be selectively mounted on liquid injector 100 with respective cylinder adapters 400.

In the above embodiment, injection head 110 has single recess 112 and single liquid syringe 200 is mounted in recess 112 with single cylinder adapter 400. However, liquid syringes 200 in various sizes and/or shapes may be mounted on an injection head (not shown) having a plurality of recesses with a plurality of respective cylinder adapters 400.

Figure 6:
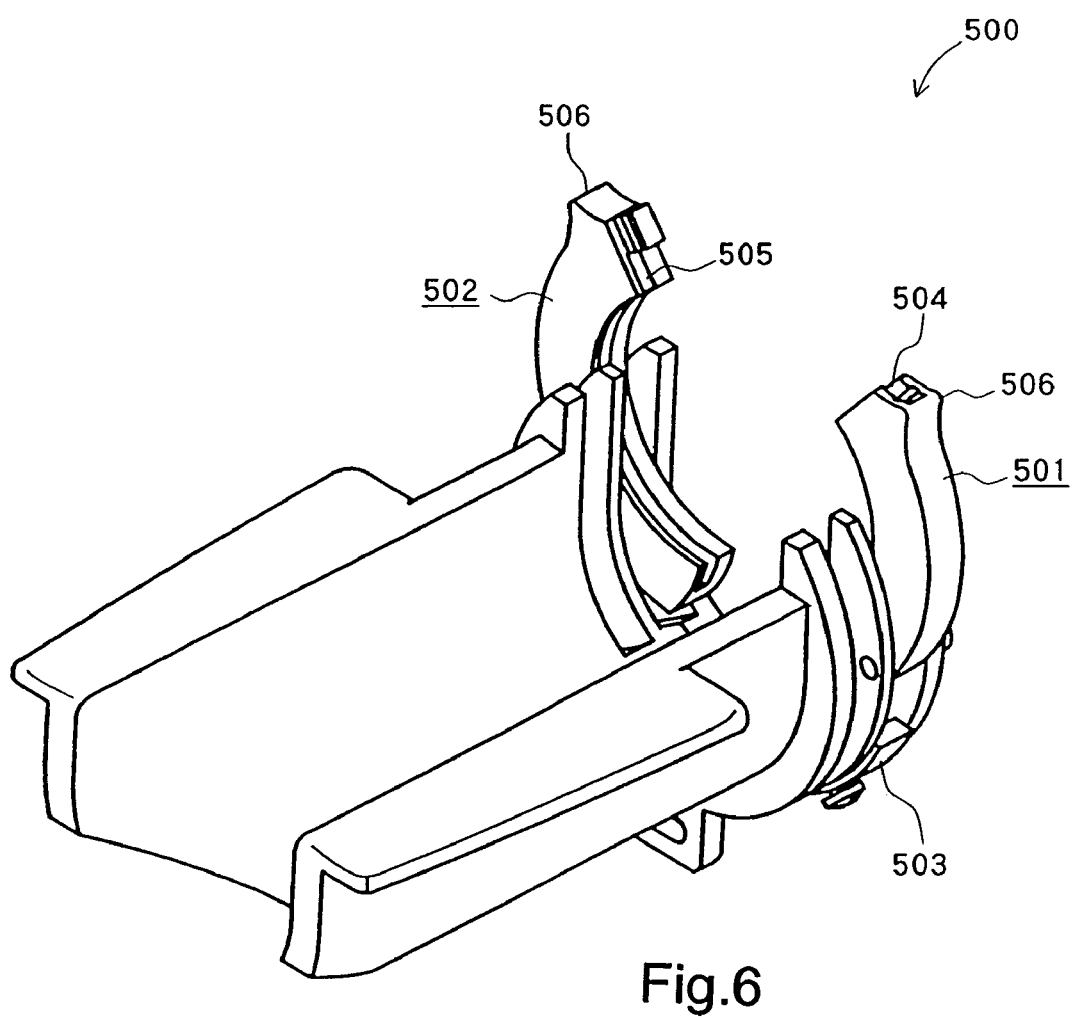
FIG. 6 is a perspective view of a cylinder adapter according to a modification.

In the above embodiment, movable holders 411 are simply angularly movably supported on cylinder adapter 400. However, as shown in FIG. 6, cylinder adapter 500 may have a pair of laterally spaced movable holders 501, 502 normally biased to an open position by a leaf spring 503 serving as a holder biasing mechanism.

With cylinder adapter 500, movable holder 501 has cavity 504 defined in an upper end thereof and movable holder 502 has tooth 505 disposed on an upper end thereof, cavity 504 and tooth 505 jointly serving as holder holding mechanism. When tooth 505 removably engages in cavity 504, movable holders 501, 502 are held in a closed position. Movable holders 501, 502 also have manually operable protrusions 506 disposed on their upper ends near cavity 504 and tooth 505, respectively.

When protrusions 506 are manually operated to turn movable holders 501, 502 into the closed position, tooth 505 engages in cavity 504, holding movable holders 501, 502 in the closed position. Liquid syringe 200 can more reliably be retained in position with cylinder adapter 500. When protrusions 506 are manually operated to displace tooth 505 out of cavity 504, movable holders 501, 502 are turned into the open position under the bias of leaf spring 503, thereby allowing liquid syringe 200 to be easily removed from cylinder adapter 500. Protrusions 506 on the upper ends of movable holders 501, 502 can be manually operated to facilitate the opening and closing of movable holders 501, 502.

In the above embodiment, liquid injector 100 can not detect when liquid syringe 200 and cylinder adapter 400 are mounted or dismounted or when movable holders 121, 141 are opened or closed. However, liquid injector 100 can have sensors (not shown) to detect when liquid syringe 200 and cylinder adapter 400 are mounted or dismounted or when movable holders 121, 141 are opened or closed.

When such sensors are incorporated into liquid injector 100, liquid injector 100 can control syringe actuating mechanism 116 so as to be operable only when liquid injector 100 detects when movable holders 121, 141 are closed, and can control syringe actuating mechanism 116 so as to be inoperable when liquid injector 100 detects when movable holders 121, 141 are opened.

While preferred embodiments of the present invention have been described using specific terms, such description is for illustrative purposes only, and it is to be understood that changes and variations may be made without departing from the spirit or scope of the following claims.

What is claimed is:

1. A liquid injection system comprising:
    a liquid syringe having a hollow cylinder with a cylinder flange disposed on the outer circumferential edge of an end thereof and a piston;
    a cylinder adapter for receiving the cylinder of said liquid syringe which is placed into the cylinder adapter from the direction substantially perpendicular to a longitudinal axial direction of said cylinder adapter; and
    a liquid injector for separately holding the cylinder of the liquid syringe with said cylinder adapter and the piston thereof, said liquid injector having a syringe actuating mechanism for moving said cylinder and said piston relatively to each other in longitudinal axial directions thereof;
    said cylinder adapter comprising:
        an adapter body having a recess for receiving said cylinder which is placed into the adapter body from the direction substantially perpendicular to a longitudinal axial direction of said adapter body;
        a pair of laterally spaced movable holders having grooves defined in inner edges thereof for receiving said cylinder flange of said liquid syringe; and
        holder pivot support mechanisms by which said movable holders are pivotally supported for movement between an open position in which said movable holders are open upwardly for allowing said cylinder flange to be inserted into said grooves, and a closed position in which said cylinder flange is retained in said grooves;
    wherein the liquid syringe has different size and can not be directly mounted on the liquid injector, and can be mounted on the liquid injector by means of the cylinder adapter; and
    wherein, in the closed position, the upper end of one movable holder is in contact with the upper end of another movable holder and the cylinder flange is fixed with the movable holders, or the movable holders and a stationary holder, all around its circumference.

2. A liquid injection system according to claim 1, wherein said cylinder adapter has a holder holding mechanism for holding said movable holders in at least said closed position.

3. A liquid injection system according to claim 2, wherein said holder holding mechanism comprises a plurality of engaging members disposed on upper ends of said movable holders for mutually disengageable engagement with each other.

4. A liquid injection system according to claim 2, wherein said cylinder adapter has a holder biasing mechanism for normally biasing said movable holders to said open position.

5. A liquid injection system according to claim 1, wherein said cylinder adapter has a stationary holder having an arcuate groove defined in an upper surface thereof for disengageably receiving a lower portion of said cylinder flange, said movable holders each being disposed on each side of said stationary holder.

6. A liquid injection system according to claim 1, wherein said movable holders have respective lower ends positioned downwardly of axes of said holder pivot support mechanisms when said movable holders are held in said closed position.

7. A liquid injection system according to claim 1, wherein said movable holders have manually operable engaging members disposed respectively on upper ends thereof.

8. A liquid injection system according to claim 1, wherein said adapter body, said movable holders, and said holder pivot support mechanisms are made of a nonmagnetic material.

9. A liquid injection system according to claim 1, wherein said liquid injector is arranged to allow said cylinder adapter to be installed thereon when said movable holders are held in said closed position, and to prevent said cylinder adapter from being installed thereon when said movable holders are held in said open position.

10. A liquid injection system according to claim 1, wherein said liquid injector comprises:
    closed-position detecting means for detecting when said movable holders of the cylinder adapter installed in the liquid injector are held in said closed position.

11. A liquid injection system according to claim 10, wherein said liquid injector comprises:
    a syringe actuating mechanism for sliding said piston; and
    control means for controlling said syringe actuating mechanism so as to be inoperable if said closed-position detecting means does not detect when said movable holders are held in said closed position.

12. A liquid injection system according to claim 1, wherein said liquid injector comprises:
    a recess for receiving a liquid syringe having a maximum size which is directly placed therein or a liquid syringe having a size other than said maximum size which is placed therein with said cylinder adapter; and
    a flange holding mechanism disposed rearwardly of said recess for removably holding the cylinder flange of said liquid syringe having the maximum size;
    said cylinder adapter having an adapter flange removable held by said flange holding mechanism.

13. A liquid injection system according to claim 1, wherein said liquid injector comprises:
    an adapter holding mechanism for securing said cylinder adapter which is removably mounted on the liquid injector.

14. A liquid injection system according to claim 13, wherein said cylinder adapter has a connector lug projecting from a lower surface thereof, said connector lug having a connector hole defined therein which is open in at least one of the longitudinal axial directions, and wherein said adapter holding mechanism comprises:
- a connector member for removably engaging in said connector hole of said cylinder adapter; and
- a member support mechanism for supporting said connector member for movement in the longitudinal axial directions.

15. A liquid injector for use in the liquid injection system according to claim 9, wherein said liquid injector is arranged to allow said cylinder adapter to be installed thereon when said movable holders are held in said closed position, and to prevent said cylinder adapter from being installed thereon when said movable holders are held in said open position.

16. A liquid injector for use in the liquid injection system according to claim 10 comprises:
- closed-position detecting means for detecting when said movable holders of the cylinder adapter installed in the liquid injector are held in said closed position.

17. A cylinder adapter for use in a liquid injection system comprising:
- an adapter body having a recess for receiving said cylinder which is placed into the adapter body from the direction substantially perpendicular to a longitudinal axial direction of said adapter body;
- a pair of laterally spaced movable holders having grooves defined in inner edges thereof for receiving said cylinder flange of said liquid syringe; and
- holder pivot support mechanisms by which said movable holders are pivotally supported for movement between an open position in which said movable holders are open upwardly for allowing said cylinder flange to be inserted into said grooves, and a closed position in which said cylinder flange is retained in said grooves;
- wherein, in the closed position, the upper end of one movable holder is in contact with the upper end of another movable holder, and the cylinder flange is fixed with the movable holders, or the movable holders and a stationary holder all around its circumference.

* * * * *